(12) United States Patent
Keitel

(10) Patent No.: US 10,751,475 B2
(45) Date of Patent: Aug. 25, 2020

(54) INJECTION DEVICE

(71) Applicant: Haselmeier AG, St. Gallen (CH)

(72) Inventor: Joachim Keitel, Esslingen (DE)

(73) Assignee: Haselmeier AG, St. Gallen (CH)

(*) Notice: Subject to any disclaimer, the term of this patent is extended or adjusted under 35 U.S.C. 154(b) by 173 days.

(21) Appl. No.: 15/942,295

(22) Filed: Mar. 30, 2018

(65) Prior Publication Data
US 2018/0221587 A1 Aug. 9, 2018

Related U.S. Application Data

(63) Continuation of application No. PCT/EP2016/001597, filed on Sep. 26, 2016.

(30) Foreign Application Priority Data

Sep. 30, 2015 (DE) .................... 20 2015 006 845 U

(51) Int. Cl.
*A61M 5/315* (2006.01)
*A61M 5/20* (2006.01)
(Continued)

(52) U.S. Cl.
CPC .......... *A61M 5/31551* (2013.01); *A61M 5/20* (2013.01); *A61M 5/3158* (2013.01);
(Continued)

(58) Field of Classification Search
CPC .................. A61M 5/3155; A61M 5/31553
See application file for complete search history.

(56) References Cited

U.S. PATENT DOCUMENTS

| 5,114,406 A | 5/1992 | Gabriel et al. |
| 5,480,387 A | 1/1996 | Gabriel et al. |

(Continued)

FOREIGN PATENT DOCUMENTS

| DE | 102007013836 A1 | 9/2008 |
| DE | 202012001411 U1 | 5/2013 |

(Continued)

OTHER PUBLICATIONS

International search report dated Jan. 17, 2017 for corresponding international application PCT/EP2016/001600.
(Continued)

*Primary Examiner* — Bhisma Mehta
*Assistant Examiner* — Rachel T. Smith
(74) *Attorney, Agent, or Firm* — Walter Ottesen, P.A.

(57) ABSTRACT

An injection device has a housing and a metering member held rotatably in the housing and fixed in the direction of a longitudinal central axis. The metering member via a threaded connection is connected to a sleeve held rotationally fixed in relation to the housing and displaceable in the direction of the axis. When setting a dosage, the metering member rotates relative to the housing, and the sleeve moves distally. When dispensing a set dosage, the sleeve moves in the proximal direction, and the metering member by virtue of the threaded connection rotates in the opposite direction. To enable an automatic injection, the device has a spring supported in relation to the injection sleeve via a first end and in relation to the housing via a second end; the spring, when squeezing out liquid, moves the sleeve proximally and on account thereof causes the set dosage to be dispensed.

12 Claims, 11 Drawing Sheets

(51) Int. Cl.
*A61M 5/24* (2006.01)
*A61M 5/31* (2006.01)

(52) U.S. Cl.
CPC . *A61M 5/31505* (2013.01); *A61M 2005/2026* (2013.01); *A61M 2005/2407* (2013.01); *A61M 2005/3126* (2013.01); *A61M 2205/581* (2013.01)

(56) References Cited

U.S. PATENT DOCUMENTS

| | | | |
|---|---|---|---|
| 6,221,053 | B1 | 4/2001 | Walters et al. |
| 9,694,136 | B2 | 7/2017 | Keitel et al. |
| 2009/0048561 | A1 | 2/2009 | Burren et al. |
| 2010/0114025 | A1 † | 5/2010 | Moller |
| 2013/0218128 | A1 | 8/2013 | Cowe |
| 2016/0151582 | A1 * | 6/2016 | Oakley .......... A61M 5/24 604/189 |
| 2016/0317749 | A1 | 11/2016 | Jugl et al. |
| 2016/0339181 | A1 | 11/2016 | Keitel |
| 2016/0346479 | A1 | 12/2016 | Keitel |
| 2016/0361499 | A1 | 12/2016 | Keitel |
| 2018/0001031 | A1 | 1/2018 | Keitel |
| 2018/0050160 | A1 | 2/2018 | Bilton et al. |
| 2018/0221586 | A1 | 8/2018 | Keitel |
| 2018/0221588 | A1 | 8/2018 | Keitel |
| 2018/0228973 | A1 | 8/2018 | Keitel |

FOREIGN PATENT DOCUMENTS

| | | |
|---|---|---|
| WO | 8907463 A1 | 8/1989 |
| WO | 2004078241 A1 | 9/2004 |
| WO | 2010000085 A1 | 1/2010 |
| WO | 2013117332 A1 | 8/2013 |
| WO | 2014166891 A1 | 10/2014 |
| WO | 2014166900 A1 † | 10/2014 |
| WO | 2014166918 A1 | 10/2014 |
| WO | 2015007816 A1 † | 1/2015 |
| WO | 2015091766 A1 | 6/2016 |

OTHER PUBLICATIONS

International search report dated Jan. 11, 2017 for corresponding international application PCT/EP2016/001599.
International search report dated Feb. 7, 2017 for international application PCT/EP2016/001597 on which this application is based.
International search report dated Dec. 16, 2016 for corresponding international application PCT/EP2016/001598.

\* cited by examiner
† cited by third party

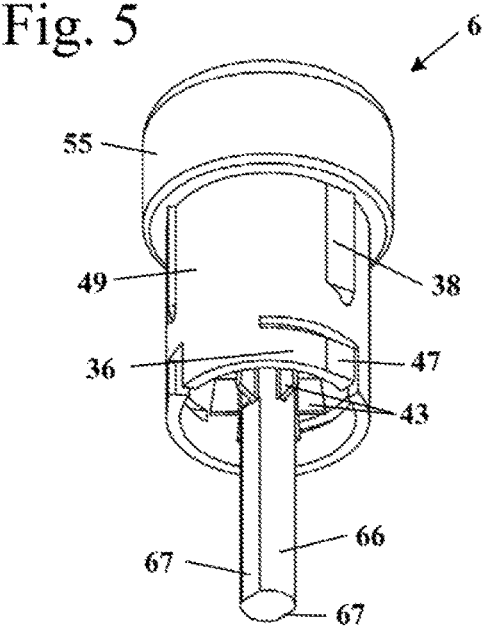
Fig. 5
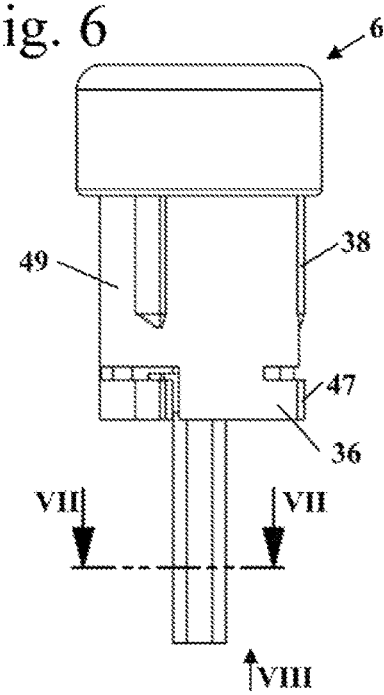
Fig. 6
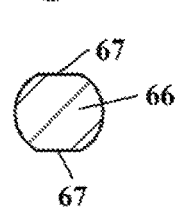
Fig. 7
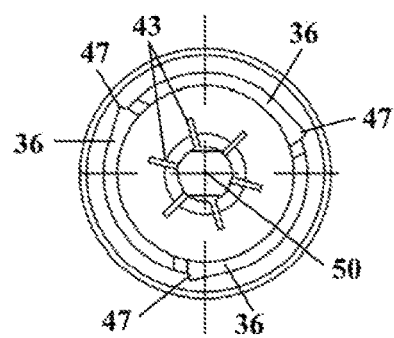
Fig. 8
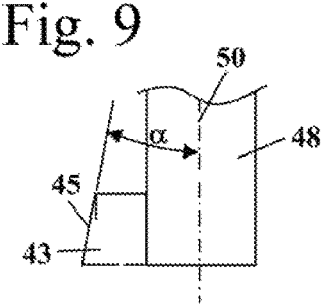
Fig. 9
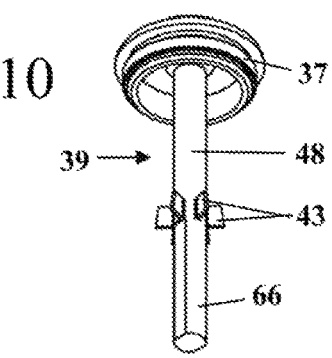
Fig. 10
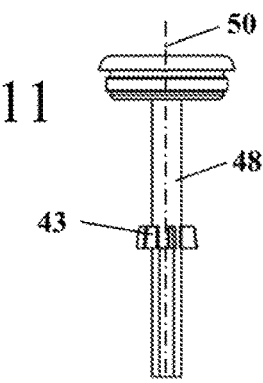
Fig. 11
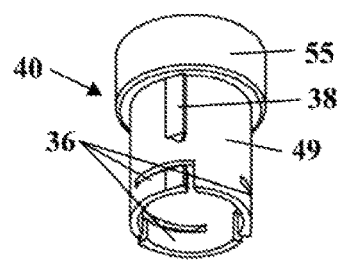
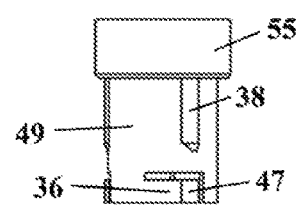

Fig. 35

Fig. 41
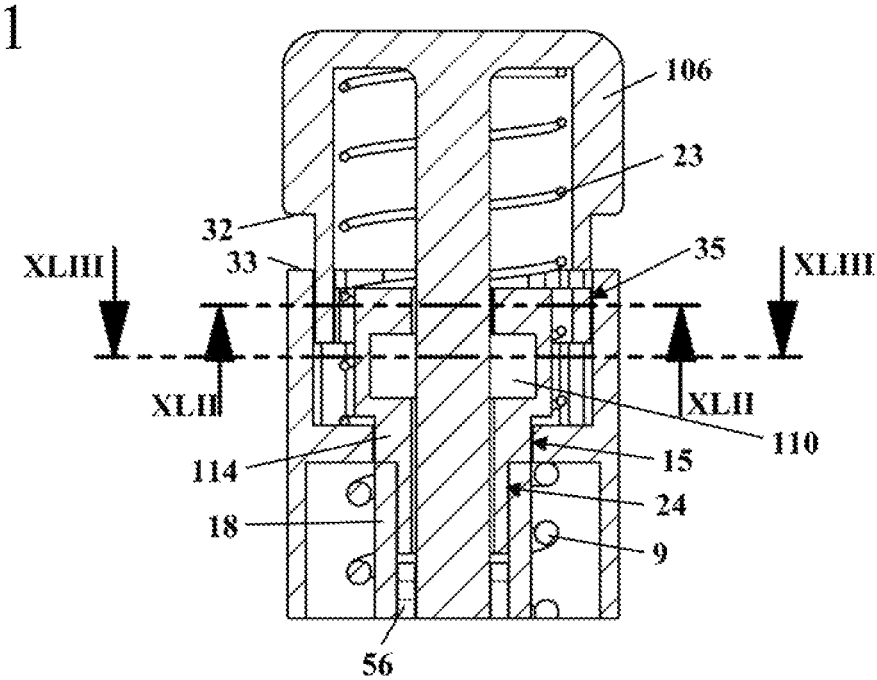
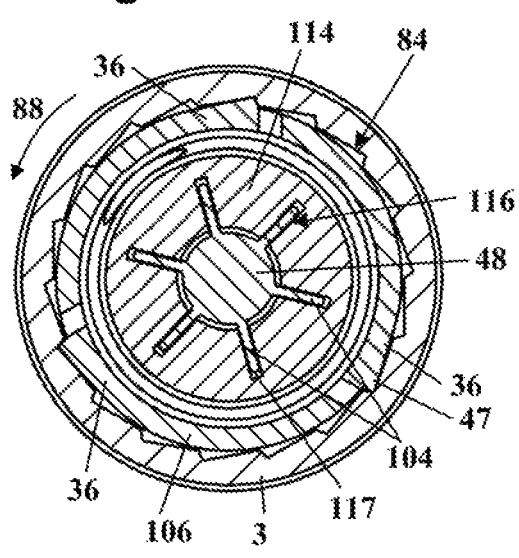
Fig. 42
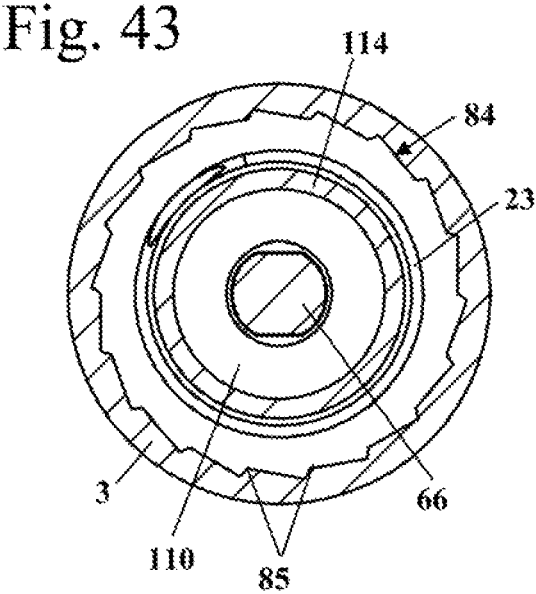
Fig. 43

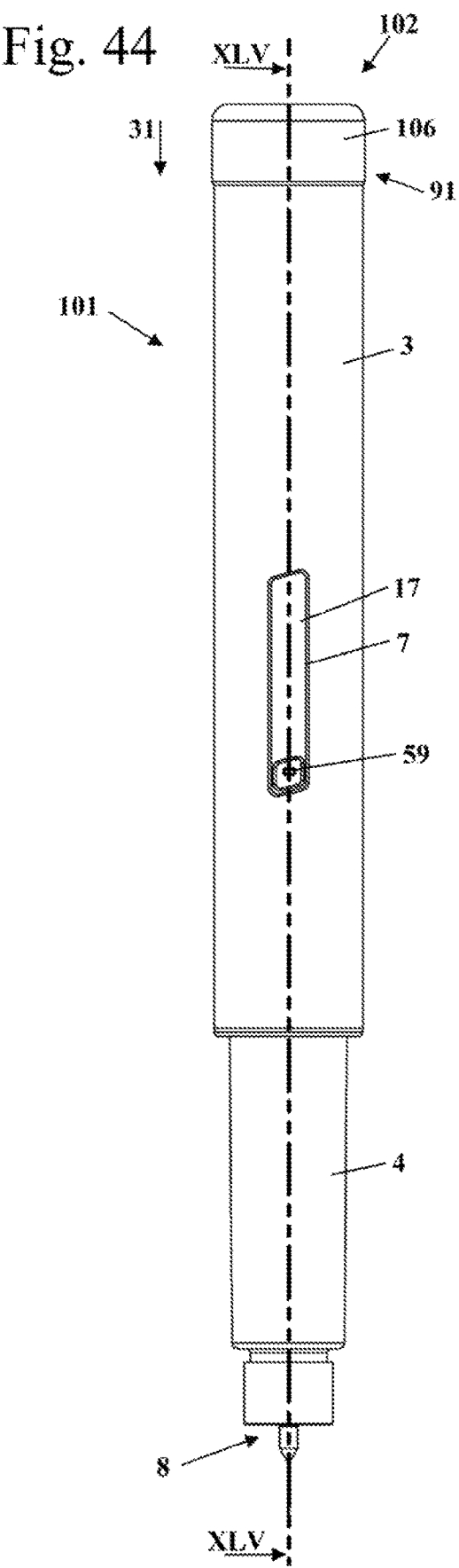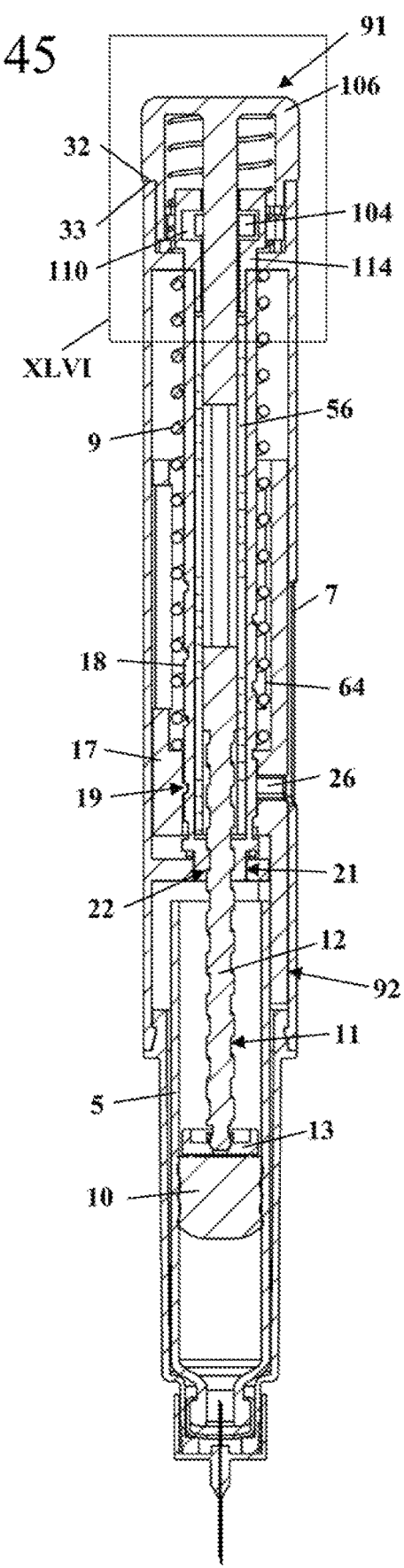

INJECTION DEVICE

CROSS REFERENCE TO RELATED APPLICATIONS

This application is a continuation application of international patent application PCT/EP2016/001597, filed Sep. 26, 2016, designating the United States and claiming priority from German application 20 2015 006 845.6, filed Sep. 30, 2015, and the entire content of both applications is incorporated herein by reference.

BACKGROUND OF THE INVENTION

An injection device of the generic type is known from WO 2013/117332 A1. The injection device has a metering member which, when setting a dosage of injection liquid to be squeezed out, is rotated in relation to the housing. An injection sleeve by way of a first threaded connection moves in the distal direction. The injection sleeve herein moves in the distal direction out of the housing. The operating button that is mounted on the injection sleeve moves conjointly with the injection sleeve in the distal direction. The operator, when squeezing out a set dosage of injection liquid, pushes the operating element in the proximal direction and, on account thereof, displaces the injection sleeve in the proximal direction. On account thereof, the metering member by virtue of the first threaded connection rotates in the opposite direction in relation to the housing, causing the injection liquid to be squeezed out from a container.

SUMMARY OF THE INVENTION

It is an object of the invention to provide an injection device, in which the injection is performed automatically.

This object can, for example, be achieved by an injection device having: a housing defining a longitudinal central axis; a metering member held in the housing so as to be rotatable and fixed in the direction of the longitudinal central axis; an injection sleeve held so as to be rotationally fixed in relation to the housing and displaceable in the direction of the longitudinal central axis; the metering member being connected to the injection sleeve via a first threaded connection; the injection device defining a distal direction and a proximal direction; wherein the metering member, when setting a dosage of injection liquid to be squeezed out, rotates in relation to the housing and the injection sleeve by virtue of the first threaded connection moves in the distal direction; wherein the metering member, when squeezing out a set dosage of injection liquid, rotates in the opposite direction in relation to the housing and the injection sleeve by virtue of the first threaded connection moves in the proximal direction; a spring having a first end and a second end; the spring being supported via the first end in relation to the injection sleeve and via the second end in relation to the housing; and, wherein the spring, when squeezing out injection liquid, moves the injection sleeve in the proximal direction and on account thereof causes the set dosage of injection liquid to be squeezed out.

It is provided that the injection device has a spring which by way of a first end is supported in relation to the injection sleeve and by way of a second end is supported in relation to the housing. Accordingly, the spring acts between two components that, when setting a dosage of injection liquid to be squeezed out or pressed out, are moved in relation to one another in the direction of the longitudinal central axis. It is provided that the spring, when squeezing out injection liquid, moves the injection sleeve in the proximal direction, on account thereof causing the set dosage of injection liquid to be squeezed out from a container. The threaded connection of the injection sleeve can be conceived such that the injection sleeve has to travel a comparatively great axial distance, and a sufficiently large tensioning distance for tensioning the spring can be guaranteed.

The distance by which the injection sleeve moves in the axial direction is capable of being set by way of the conception of the first threaded connection such that an adaptation to the desired tensioning distance is enabled in a simple manner.

The spring is advantageously configured as a compression spring. The spring herein is in particular a compression coil spring. A configuration of the spring as a tension spring, in particular as a tension coil spring, can however also be advantageous. A simple construction results when the spring by way of the first end thereof is supported directly on the injection sleeve, and by way of the second end thereof is supported on the housing. The spring accordingly acts directly between the injection sleeve and the housing. However, it can also be advantageous for the spring to be supported on a component that is connected to the injection sleeve and/or to the housing.

A compact construction is achieved when the metering member is disposed radially within the injection sleeve. The spring is advantageously disposed on the external circumference of the metering member and at least partially in an annular space that is formed between the metering member and the injection sleeve.

In order for a set dosage to be read in a simple manner, it is provided that the housing has a viewing window, and that the injection sleeve has an opening which superposes the viewing window and through which a scale that is disposed on the external circumference of the metering member is visible. In order for an unequivocal display of the set dosage to be achieved even in the case of a large axial distance of the injection device and of a plurality of revolutions of the metering member up to the maximum dosage that can be set, it is provided that the injection sleeve has a portion which at the maximum dosage set covers the proximal region of the viewing window. In order to achieve a small construction length of the injection device, it is advantageously provided that the portion which covers the proximal region of the viewing window is configured on a web of the injection sleeve which protrudes in the proximal direction. The web herein advantageously extends only in the region of the viewing window, thus not across the entire circumference of the injection device. It is provided that the injection device comprises a container having an injection liquid. In the zero position of the injection device, thus when no quantity of injection liquid to be squeezed out or pressed out has been set, the web advantageously protrudes into the region of the container. A pocket into which the web in the zero position protrudes is advantageously formed in the radial direction between the container and an upper housing part of the injection device. On account of the web and the container mutually overlapping in the axial direction, a comparatively minor construction length of the injection device can be achieved.

The housing advantageously has a housing wall on which a pivot bearing for the metering member is configured. The housing wall advantageously runs so as to be approximately perpendicular to the longitudinal central axis. The web in the zero position advantageously protrudes through a passage opening in the housing wall onto the proximal side of the housing wall. The container is advantageously disposed, and the pocket for the web is advantageously configured, on the proximal side of the housing wall.

It is provided that the injection sleeve in each position of the injection device is disposed completely in the housing of the injection device. A movement of the injection sleeve in the distal direction out of the housing is advantageously not provided.

The injection device advantageously has an operating element which, when setting the dosage of injection liquid to be squeezed out, by way of a first coupling is connected in a rotationally fixed manner to the metering member and, when squeezing out a set dosage of injection liquid, by way of a second coupling is connected in a rotationally fixed manner to the housing and is rotatable in relation to the metering member. The operating element, when setting the dosage, is advantageously in a distal terminal position. The operating element, when setting the dosage, is accordingly not moved conjointly with the injection sleeve in the distal direction. In order for the first coupling to be released, the operating element is advantageously to be moved in the proximal direction. Releasing the first coupling herein corresponds to releasing the injection, since the metering member in the case of the released first coupling is rotatable in relation to the operating element and thus in relation to the housing, the spring being able to move the injection sleeve in the proximal direction and herein to rotate the metering member.

A metering piston which by way of a second threaded connection is connected to the metering member is advantageously provided for squeezing out injection liquid from the container. The metering piston, when setting the quantity of injection liquid to be squeezed out, is advantageously connected in a rotationally fixed manner to the metering member and rotates conjointly with the metering member. The metering piston, when squeezing out a quantity of injection liquid to be squeezed out, is advantageously connected in a rotationally fixed manner to the housing and by virtue of the second threaded connection moves in the proximal direction. A simple construction of the injection device is achieved on account thereof.

BRIEF DESCRIPTION OF THE DRAWINGS

The invention will now be described with reference to the drawings wherein:

FIG. 5 shows a perspective illustration of the operating element of the injection device from FIGS. 1 to 4;

FIG. 6 shows a lateral view of the operating element from FIG. 5;

FIG. 7 shows a section along the line VII-VII in FIG. 6;

FIG. 8 shows a view of the operating element in the direction of the arrow VIII in FIG. 6;

FIG. 9 shows a schematic illustration of a latching web of the operating element;

FIG. 10 shows a schematic perspective illustration of the operating element in two individual parts;

FIG. 11 shows a lateral view of the two individual parts of the operating element;

FIG. 35 shows a lateral view of an upper housing part of the injection device;

FIG. 41 shows the fragment XLI from FIG. 40 in an enlarged illustration;

FIG. 42 shows a section along the line XLII-XLII in FIG. 41;

FIG. 43 shows a section along the line XLIII-XLIII in FIG. 41;

FIG. 44 shows a lateral view of the injection device in a terminal position upon squeezing out a set dosage of injection liquid;

FIG. 45 shows a section along the line XLV-XLV in FIG. 44;

DESCRIPTION OF THE PREFERRED EMBODIMENTS OF THE INVENTION

Figure 1:
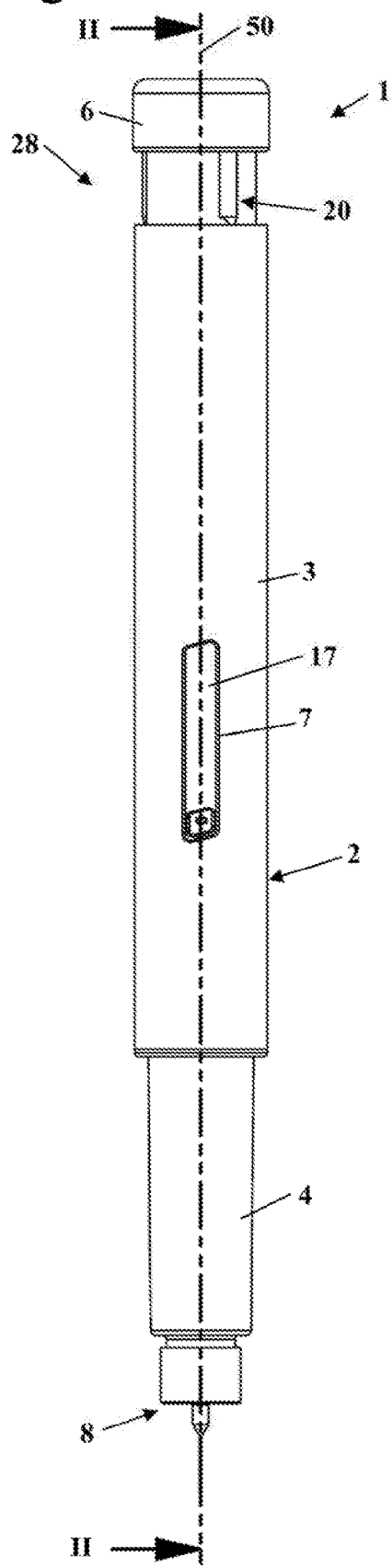
FIG. 1 shows a lateral view of an injection device in the zero position.

FIG. 1 shows an injection device 1 as an embodiment of a mechanical injection device in which the squeezing out of a dosage of injection liquid is performed automatically. The injection device 1 has a housing 2 which comprises an upper housing part 3 and a holder 4 which is secured on an upper housing part 3. The holder 4 is disposed on the proximal side of the upper housing part 3. An injection needle 8 is secured on the proximal side of the holder 4. An operating element 6 is disposed on the distal side of the injection device 1. The operating element 6 by way of a coupling 20 is connectable in a rotationally fixed manner to the upper housing part 3. The upper housing part 3 has a viewing window 7 which is advantageously composed of a transparent material such that an injection sleeve 17 that is disposed in the upper housing part 3 is visible through the viewing window 7. The injection device 1 has a longitudinal central axis 50 which runs in the longitudinal direction of the housing 2 of the injection device 1.

The distal end of the injection device 1 is that end that faces away from an injection needle 8 that is held on the injection device 1. "Proximal" refers to that side of the injection device 1 which in an injection faces the pierced location, and "distal" refers to that side that faces away from the pierced location. The proximal direction describes the injection direction, thus the direction toward the injection needle 8, or the direction in which the injection liquid is squeezed out from a container, respectively. The distal direction describes the opposite direction, thus away from the injection needle 8.

Figure 2:
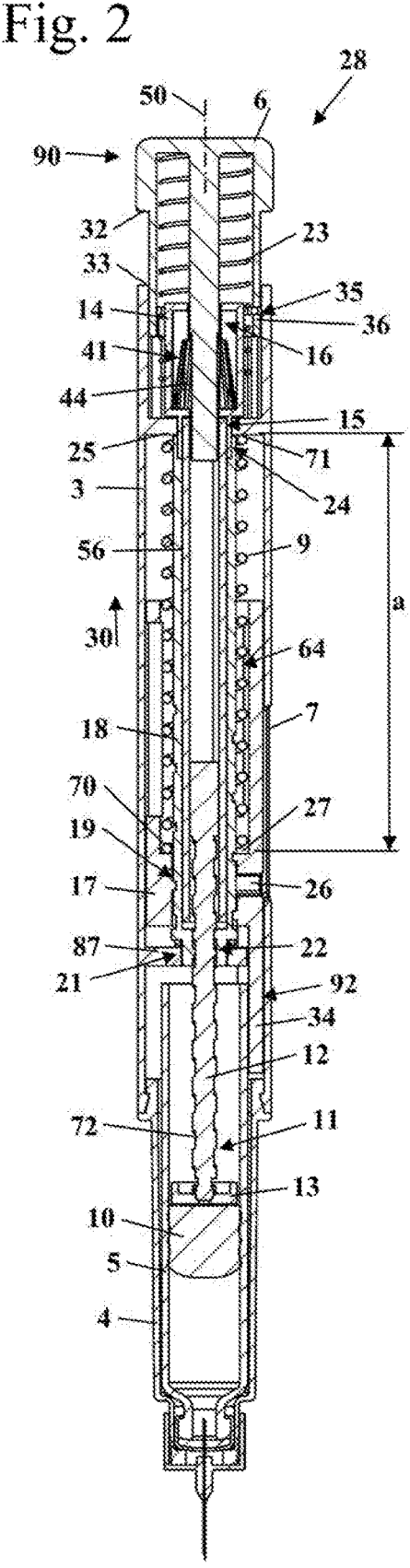
FIG. 2 shows a section along the line II-II in FIG. 1.

FIGS. 1 and 2 show the injection device 1 in a zero position 28 at which no dosage of injection liquid is set. The operating element 6 is in the distal terminal position 90 thereof. As is shown in FIG. 2, a container 5 having an injection liquid is disposed in the holder 4. A plug 10 is disposed in the container 5, a piston disk 13 of a metering piston 11 bearing on the plug 10. The metering piston 11 moreover comprises a piston rod 12 which supports an external thread 72.

The external side of the injection sleeve 17 is visible through the viewing window 7 of the upper housing part 3. The injection sleeve 17 has an opening 26 through which the external circumference of a metering member 18 that is disposed radially within the injection sleeve 17 is visible. The metering member 18 which can also be referred to as a graduated tube, on the external circumference thereof supports a scale 59 (shown in FIG. 30) which is visible to the operator through the viewing window 7 and through the opening 26, and displays the set dosage of injection liquid to be squeezed out.

The injection sleeve 17 is held in the upper housing part 3 so as to be displaceable in the direction of the longitudinal central axis 50 and so as to be rotationally fixed in relation to the upper housing part 3. The injection sleeve 17 herein is disposed completely within the housing 2, specifically within the upper housing part 3, in each position of the injection device 1. The metering member 18 and the injection sleeve 17 are interconnected by way of a first threaded connection 19. The metering member 18 is mounted on a pivot bearing 21 so as to be rotatable in the upper housing part 3, and held so as to be axially non-displaceable in the upper housing part 3. The metering member 18 by way of a second threaded connection 22 is connected to the external thread 72 of the piston rod 12.

An entrainment element 14 is mounted in the upper housing part 3. The entrainment element 14 is connected in a rotationally fixed manner to the metering member 18 by way of a rotationally fixed connection 24. The rotationally fixed connection 24 can be a press-fit connection. However, it can also be provided that the rotationally fixed connection 24 is a form-fitting connection. The entrainment element 14 is rotatably mounted on a pivot bearing 15 that is configured in an upper housing part 3. The pivot bearing 15 is formed by a periphery of the upper housing part 3.

As is also shown in FIG. 2, a spring 9 which is configured as a compression spring, specifically as a compression coil spring, is disposed in the upper housing part 3. The spring 9 by way of a first end 70 is supported on a bearing periphery 27 of the injection sleeve 17, and by way of a second end 71 is supported on a bearing periphery 25 of the upper housing part 3. The pivot bearing 15 for the entrainment element 14 is also configured on the bearing periphery 25. The spring 9 is disposed so as to be radially outside the metering member 18, and in the zero position 28 shown in FIG. 2, by way of the proximal region of the spring 9, protrudes into an annular space 64 that is formed between the injection sleeve 17 and the metering member 18.

The operating element 6 is connected in a rotationally fixed manner to the piston rod 12 by way of a connection element 56 which is configured as a sleeve. The operating element 6 is supported in relation to the upper housing part 3 by way of a spring 23 which is configured as a compression coil spring. The spring 23, which pushes the operating element 6 in the distal direction, has no influence on the injection rate. The spring 23 is conceived merely such that the operator can activate the operating element 6 by way of a comfortable force. A shoulder 32 which, in the case of an operating element 6 that is pushed in the proximal direction, interacts with a periphery 33 of the upper housing part 3 is configured on the operating element 6, the shoulder 32 conjointly with the periphery 33 forming a detent which delimits the proximal position of the operating element 6. A further detent which can be configured on the entrainment element 14, for example, is advantageously provided for establishing the distal terminal position 90 of the operating element 6. A latching installation 35 which comprises a plurality of latching arms 36, one of which being visible in FIG. 2, acts between the operating element 6 and the upper housing part 3. The operating element 6 in the zero position 28 shown in FIGS. 1 and 2 is coupled in a rotationally fixed manner to the entrainment element 14 by way of a coupling 16. Moreover, a setting device 41 which comprises a multiplicity of latching depressions 44 in the entrainment element 14 is formed between the operating element 6 and the entrainment element 14.

In the case of a non-activated operating element 6, the spring 23 pushes the operating element 6 to the distal terminal position 90 thereof, in which the coupling 20 is opened and the operating element 6 is rotatable in relation to the housing 2. In order to set a quantity of injection liquid to be squeezed out, the operator rotates the operating element 6 about the longitudinal central axis 50. The entrainment element 14 that by way of the coupling 16 is connected in a rotationally fixed manner to the operating element 6 is conjointly rotated herein. The entrainment element 14 by way of the rotationally fixed connection 24 is connected to the metering member 18 which is likewise conjointly rotated. The piston rod 12 by way of the connection element 56 is connected in a rotationally fixed manner to the operating element 6 and is likewise conjointly rotated. The injection sleeve 17, by virtue of the first threaded connection 19 and of the fixing of the injection sleeve 17 in a rotationally fixed manner in the upper housing part 3, is moved in the distal direction 30 in the rotating movement of the metering member 18. The injection sleeve 17, by way of the bearing periphery 27 thereof, herein moves toward the bearing periphery 25 of the spring 9, on account of which the spring 9 is tensioned. The bearing periphery 25 of the housing 2 herein can form a detent for the distal position of the injection sleeve 17, thus also for the maximum dosage that can be set. The axial position of the operating element 6 is not changed when the dosage of injection liquid to be squeezed out is set. The length of the annular space 64 has been shortened by virtue of the movement of the injection sleeve 17 in the distal direction.

Figure 3:
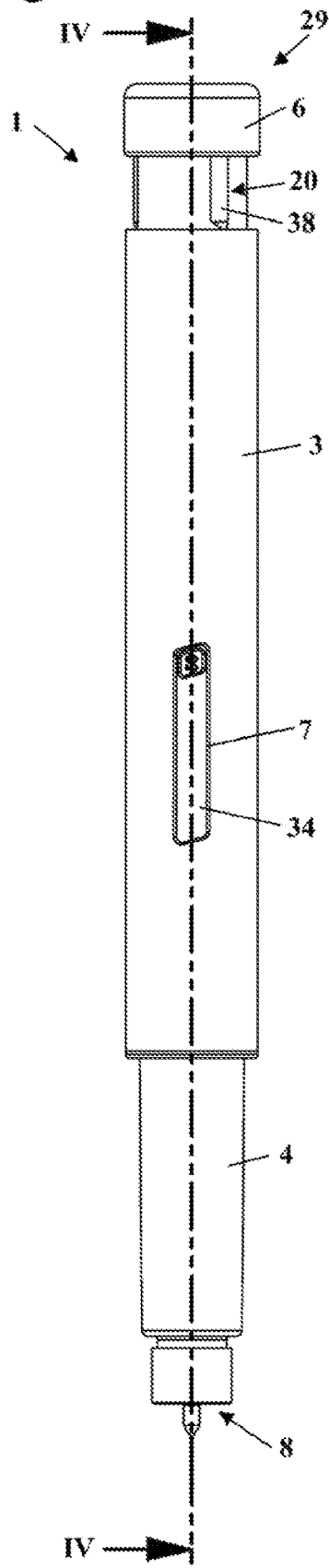
FIG. 3 shows a lateral view of the injection device from FIG. 1 in the maximum position.
Figure 4:
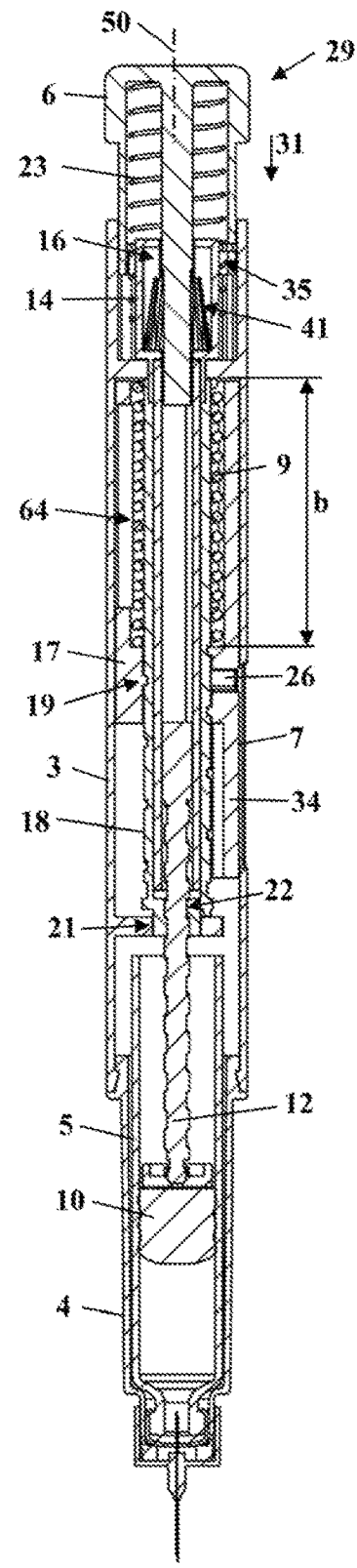
FIG. 4 shows a section along the line IV-IV in FIG. 1.
Figure 12:
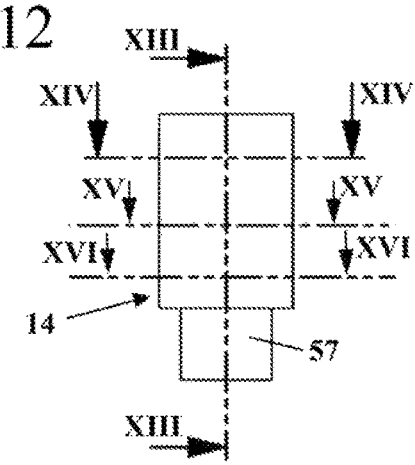
FIG. 12 shows a lateral view of the entrainment element of the injection device.

FIGS. 3 and 4 show the injection device 1 in a maximum position 29 at which the maximum dosage is set. The length of the spring 9 has been shortened from the non-tensioned length a, shown in FIG. 2, to the tensioned length b, shown in FIG. 4. It can also be provided that the spring 9 is pretensioned also in the zero position 28. The injection sleeve 17 can bear on the bearing periphery 25. The spring 9 in the maximum position 29 in the embodiment is disposed completely in the annular space 64. As is shown in FIG. 3, the maximum dosage is visible through the viewing window 7 in the maximum position 29. The injection sleeve 17 has a web 34 which protrudes in the proximal direction and covers the region of the metering member 18 that is visible through the viewing window 7 and that does not display the set dosage. A pocket 92 into which the web 34 in the zero position 28 protrudes is formed in the radial direction between the container 5 and the upper housing part 3. The web 34 herein protrudes through a housing wall 87 of the upper housing part 3 onto the proximal side of the housing wall 87. The pivot bearing 21 for the metering member 18 is configured on the housing wall 87. The threaded connection 22 between the piston rod 12 and the metering member 18 is also disposed in the region of the housing wall 87.

Figure 38:
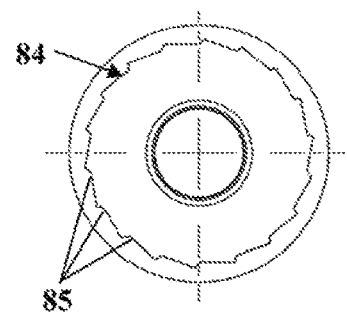
FIG. 38 shows a lateral view in the direction of the arrow XXXVIII in FIG. 36.

In order for a set quantity of injection liquid to be squeezed out, the operator pushes the operating element 6 in the proximal direction 31. On account thereof, webs 38 of the coupling 20 (FIG. 1) come to engage with latching elements 85 of the latching installation 35 (FIG. 38). On account thereof, the operating element 6 in relation to the upper housing part 3 is fixed in a rotationally fixed manner. At the same time, the coupling 16 by virtue of the axial relative movement of the operating element 6 in relation to the entrainment element 14 is at least partially released such that the entrainment element 14, conjointly with the metering member 18, can rotate about the longitudinal central axis 50. The rotating movement is performed by virtue of the axial force that is exerted by the tensioned spring 9 on the injection sleeve 17, the force causing a rotation of the metering member 18. The rotation is performed by virtue of the threaded connection 19 and of the injection sleeve 17 being guided in a rotationally fixed manner in the housing part 3. The piston rod 12 is connected in a rotationally fixed manner to the upper housing part 3 by way of the connection element 56 and of the operating element 6. Therefore, the second threaded connection 22 in the rotation of the metering member 18 causes a movement of the piston rod 12 in the proximal direction 31. On account thereof, the set quantity of injection liquid is squeezed out from the container 5.

By virtue of the force stored in the spring 9, the injection is performed automatically upon releasing the coupling 16. The spring 9 is conceived such that the force stored in the spring 9 is sufficient in order for the resistance of the plug 10 to be overcome and for injection liquid to be squeezed out from the container 5. The injection device 1 has the setting device 41 in order for the injection rate to be set. The setting device 41 influences the torque that is required for rotating the entrainment element 14 in relation to the operating element 6. The torque required herein depends on the axial position of the operating element 6 in relation to the upper housing part 3 and to the entrainment element 14. This will be explained in yet more detail hereunder.

FIGS. 5 to 11 show the construction of the operating element 6 in detail. The operating element 6 has an operating portion 55 which protrudes from the upper housing part 3, the operator being able to rotate the operating element 6 or to displace the latter in the proximal direction 31 at the operating portion 55. The operating element 6 has a sleeve portion 49 (shown in FIGS. 5 and 6) which in the zero position 28 and the maximum position 29 protrudes partially from the upper housing part 3, the webs 38 of the coupling 20 being fixed to the sleeve portion 49. The sleeve portion 49 on the proximal end thereof supports a total of three latching arms 36 which at the free end thereof have in each case one latching element 47.

This is also shown in FIG. 8. The outwardly protruding latching elements 47 by way of the latching arms 36 are mounted so as to be movable in a radially inward manner.

Figure 17:
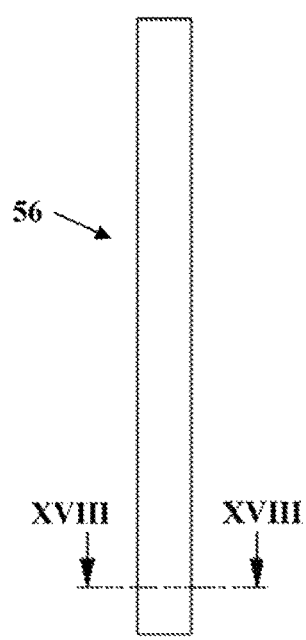
FIG. 17 shows a lateral view of the connection element of the injection device.
Figure 18:
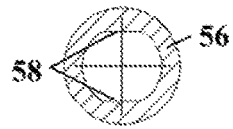
FIG. 18 shows a section along the line XVIII-XVIII in FIG. 17.
Figure 20:
FIG. 20 shows a section along the line XX-XX in FIG. 19.
Figure 21:
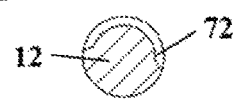
FIG. 21 shows a section along the line XXI-XXI in FIG. 19.
Figure 19:
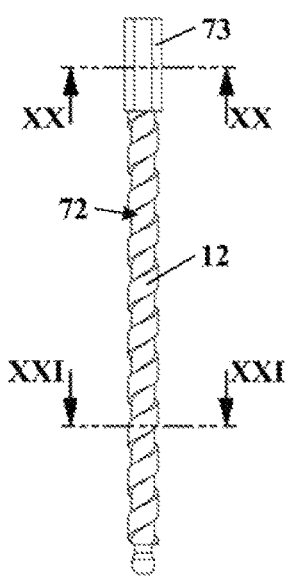
FIG. 19 shows a lateral view of a piston rod of the injection device.

As is also shown in FIG. 5, the operating element 6 has a connector 66 which on the external circumference thereof supports two bevels 67 for connecting in a rotationally fixed manner to the connection element 56. As is shown in FIGS. 17 and 18, the connection element 56, which is configured so as to be sleeve-shaped, on the internal side thereof has corresponding bevels 58 which interact with the bevels 67 of the connector 66 and, on account thereof, interconnect in a rotationally fixed manner the operating element 6 and the connection element 56. As is shown in FIGS. 19 and 20, the piston rod 12 on a distal end portion 73 supports corresponding bevels 74 in order for the piston rod 12 and the connection element 56 to be connected in a rotationally fixed manner. The external thread 72 of the piston rod 12 is also shown in FIGS. 19 and 21.

Figure 25:
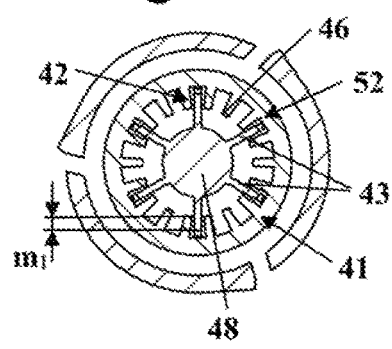
FIG. 25 shows a section along the line XXV-XXV in FIG. 24.

As is shown in FIGS. 5 and 8, the operating element 6 in the embodiment has six latching webs 43 which in relation to the longitudinal central axis 50 protrude in a radially outward manner and which conjointly with the latching depressions 44 of the entrainment element 14 form a latching installation 42 (FIG. 25). As is schematically shown in FIG. 9, each latching web 43 has a radially outward latching edge 45. The latching edges 45 in the embodiment are inclined in relation to the longitudinal central axis 50 by an angle α. The angle α is adapted to the desired activation distance between the slowest and the fastest injection rate that can be set, and to the desired difference between the slowest and the fastest injection rate. As is schematically shown in FIG. 9, the latching webs 43 are disposed on a pin portion 48 of the operating element 6, the pin portion 48 running within the sleeve portion 49 at a radial spacing from the sleeve portion 49. The connector 66 adjoins the pin portion 48 at the proximal end. The latching webs 43 in the embodiment are configured so as to be integral to the operating element 6 and are composed of the same material as the operating element 6. However, it can also be advantageous for the latching webs 43 to be configured from another material, for example from an elastomer or a rubber, in order for a desired latching characteristic to be set.

As is shown in FIGS. 10 and 11, the operating element 6 is constructed from a first individual part 39 and from a second individual part 40, in order for the production and the assembly to be simplified. The operating element 6 can also be formed from a larger number of individual parts. The individual parts 39 and 40 in the embodiment are fixedly interconnected at a latching periphery 37 of the first individual part 39.

Figure 13:
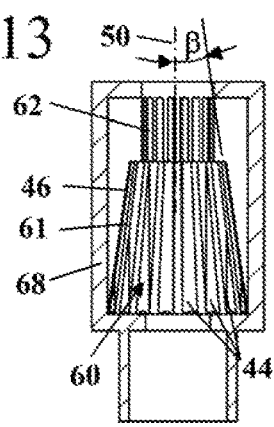
FIG. 13 shows a section along the line XIII-XIII in FIG. 12.
Figure 14:
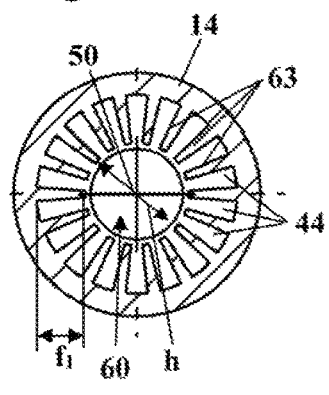
FIG. 14 shows a section along the line XIV-XIV in FIG. 12.

FIGS. 12 to 16 show the configuration of the entrainment element 14 in detail. The entrainment element 14 has a bearing portion 57 having a reduced diameter, by way of which the entrainment element 14 is rotatably mounted in the upper housing part 3. As is shown in FIG. 13, the entrainment element 14 in the interior thereof has a conical portion 61 which is disposed in a proximal region, a cylindrical portion 62 adjoining the conical portion 61 on the distal side of the latter. The conical portion 61 and the cylindrical portion 62 are formed by a multiplicity of webs 63 (shown in FIGS. 14 to 16) which protrude in a radially inward manner from a cylindrical external wall 68 of the entrainment element 14. The latching depressions 44 are formed in the circumferential direction between the webs 63. The webs 63 have radially inward counter latching edges 46 which are inclined in relation to the longitudinal central axis 50 by an angle β. The angle β herein is open toward the proximal direction. In particular, the angle β is the same size as the angle α of the latching edges 45 of the latching webs 43.

The webs 63 in the cylindrical portion 62 delimit an interior space 60, the interior diameter h of the latter (shown in FIG. 14) being only slightly larger than the external diameter of the pin portion 48. The webs 63 in the cylindrical portion 62 have a radially measured height $f_1$ that corresponds to approximately the radial extent of the latching webs 43.

Figure 15:
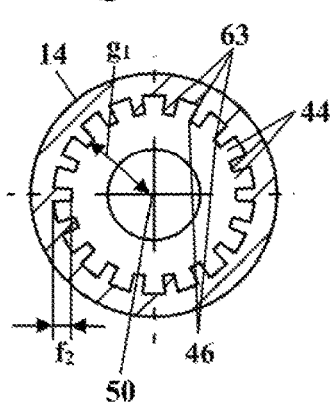
FIG. 15 shows a section along the line XV-XV in FIG. 12.

FIG. 15 shows a section through the conical portion 61. The radially inward latching edges 46 of the webs 63 in the section plane shown in FIG. 15 have a spacing $g_1$ from the longitudinal central axis 50. The radially measured height $f_2$ of the webs 63 in the section plane through the conical portion 61 shown in FIG. 15 is significantly smaller than the height $f_1$ in the cylindrical portion 62.

Figure 16:
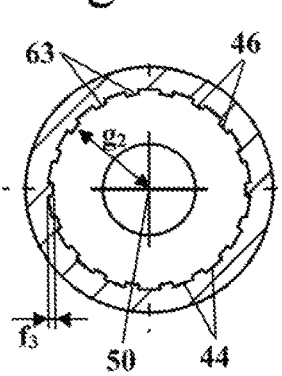
FIG. 16 shows a section along the line XVI-XVI in FIG. 12.

FIG. 16 shows a section through the conical portion 61, adjacent to the proximal end of the interior space 60. The latching edges 46 in this section plane have a spacing $g_2$ from the longitudinal central axis 50 which is significantly larger than the spacing $g_1$. The radially measured height $f_3$ of the webs 63 in the section plane through the conical portion 61 shown in FIG. 15 is significantly smaller than the height $f_2$ in the distal section plane shown in FIG. 15.

Figure 22:
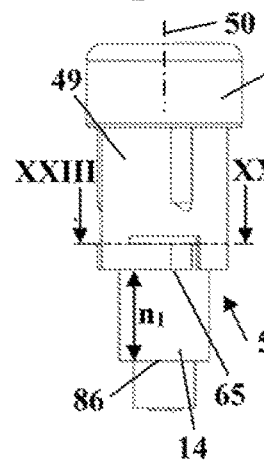
FIG. 22 shows a lateral view of the operating element and of the entrainment element in a coupling position.
Figure 23:
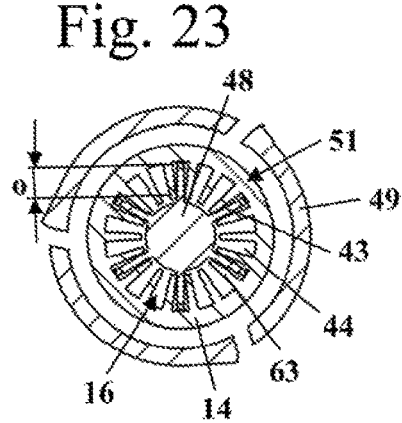
FIG. 23 shows a section along the line XXIII-XXIII in FIG. 22.

FIGS. 22 to 29 show the operating element 6 and the entrainment element 14 in different axial relative positions. FIGS. 22 and 23 show the operating element 6 and the entrainment element 14 in a coupling position 51. In this position, the operating element 6 and the entrainment element 14 are interconnected in a rotationally fixed manner by way of the coupling 16. The coupling 16 is formed by the webs 63 in the cylindrical portion 62. The webs 63 protrude up close to the pin portion 48 and overlap the latching webs 43 on the distal side thereof in the circumferential direction by an engagement depth o. The engagement depth o is chosen such that the entrainment element 14 and the operating element 6 are interconnected in a rotationally fixed manner. FIGS. 23, 25, 27, and 29 herein show sections through the operating element 6 on the distal side of the latching webs 43. The sleeve portion 49 has a proximal end side 65. The proximal end side 65 in the coupling position 51 has a first spacing $n_1$, measured from a lower edge 86 of the entrainment element 14 in the direction of the longitudinal central axis 50. The lower edge 86 herein is that edge of the entrainment element 14 that bears on the inwardly protruding periphery of the upper housing part 3.

Figure 24:
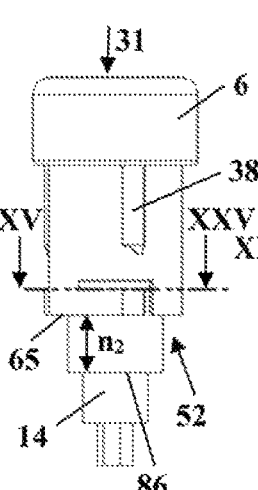
FIG. 24 shows a lateral view of the operating element and of the entrainment element in a first relative position.

FIGS. 24 and 25 show the operating element 6 and the entrainment element 14 in a first relative position 52, at which the setting device 41 acts between the operating element 6 and the entrainment element 14. The proximal end side 65 of the sleeve portion 49 has a spacing $n_2$ from the lower edge 86 of the entrainment element 14 which is smaller than the spacing $n_1$. As is shown in FIG. 25, the latching webs 43 are in the conical portion 61 in which the spacing of the latching edges 46 of the webs 63 from the pin portion 48 and from the longitudinal central axis 50 is reduced. In this relative position, the latching webs 43, on the distal side of the latching webs 43, overlap the webs 63 in the radial direction by a latching depth $m_1$. The latching depth $m_1$ is significantly smaller than the engagement depth o in the coupling position 51. The latching depth $m_1$ is chosen such that the entrainment element 14 can rotate in relation to the operating element 6 while deforming the latching webs 43.

In order to reach the first relative position 52 from the coupling position 51, the operator has to move the operating element 6 in the proximal direction 31, as is indicated in FIG. 24. On account thereof, the operating element 6 is displaced relative to the upper housing part 3, and the webs 38 on the operating element 6 come to engage with a latching mechanism 84 (shown in FIGS. 36 and 38) on the internal side of the upper housing part 3. The latching mechanism 84 has a multiplicity of latching elements 85 which secure the operating element 6 in a rotationally fixed manner in relation to the external housing part 3. The webs 38, conjointly with the latching mechanism 84, form the coupling 20.

In the case of the first relative position 52, shown in FIGS. 24 and 25, the entrainment element 14 can rotate relative to the upper housing part 3 and relative to the operating element 6 when the energy stored in the spring 9 is sufficient in order for the latching webs 43 to be deformed and for the plug 10 to slide in the proximal direction such that the injection liquid is squeezed out from the container 5. However, by virtue of the high torque that is required for rotating the entrainment element 14 in relation to the operating element 6, the squeezing out of injection liquid is performed very slowly.

Figure 26:
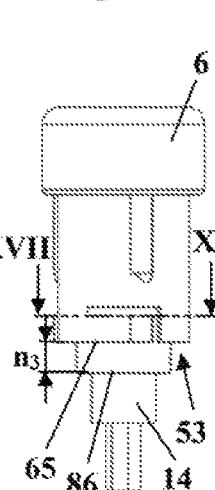
FIG. 26 shows a lateral view of the operating element and of the entrainment element in a second relative position.
Figure 27:
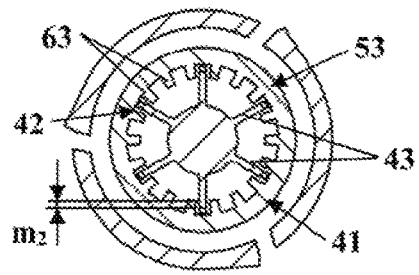
FIG. 27 shows a section along the line XXVII-XXVII in FIG. 26.

In the second relative position 53, shown in FIGS. 26 and 27, of the operating element 6 and of the entrainment element 14, the operator has pushed the operating element 6 in the proximal direction 31 further into the upper housing part 3. The proximal end side 65 in this position has a third spacing $m_3$ from the lower edge 86 of the entrainment element 14. The third spacing $m_3$ is significantly smaller than the second spacing $m_2$. In the movement of the operating element 6 in the proximal direction 31 the latching webs 43 in the conical portion 61 have moved further in the proximal direction, thus in the direction toward an enlarged internal diameter of the conical portion 61. The distal side of the latching webs 43 in the radial direction toward the longitudinal central axis 50 has a minor overlap in relation to the webs 63, such that only a minor latching depth $m_2$ results. In this position of the setting device 41, the torque required for rotating the entrainment element 14 in relation to the operating element 6 is significantly smaller than in the case of the first relative position 52 shown in FIGS. 24 and 25. The latching webs 43 have to be only slightly deformed in order for the webs 63 to be overcome and for the next latching position to be reached. On account thereof, an injection at the second relative position shown in FIGS. 26 and 27 is performed at a higher rate than in the case of the first relative position shown in FIGS. 24 and 25.

Figure 28:
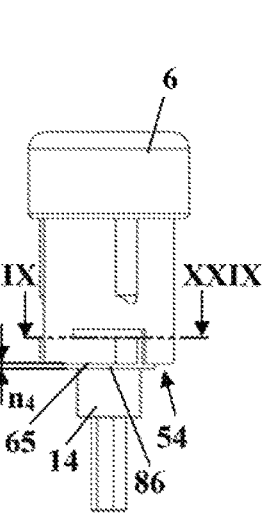
FIG. 28 shows a lateral view of the operating element and of the entrainment element in a third relative position.
Figure 29:
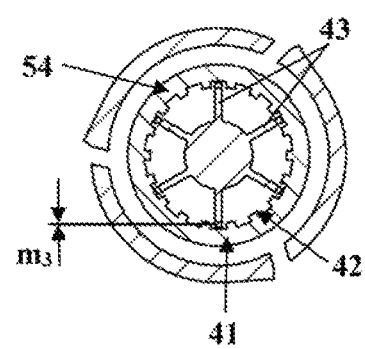
FIG. 29 shows a section along the line XIX-XIX in FIG. 28.

FIGS. 28 and 29 show the operating element 6 and the entrainment element 14 in a third relative position 54 in which the lower edge 86 has only a very minor fourth spacing n, from the proximal end side 65. The operating element 6 is in the proximal terminal position thereof in the third relative position 54, in which the shoulder 32 (shown in FIG. 2) bears on the periphery 33 of the upper housing part 3. As is shown in FIG. 29, the latching webs 43 in the third relative position 54 in the radial direction have an extremely minor overlap in relation to the webs 63. The latching depth $m_3$ is minimal. It can also be provided that the latching depth $m_3$ is zero, such that the latching webs 43 can freely rotate in relation to the webs 63, and the setting device 41 in the third relative position 54 does not slow down the rotation of the entrainment element 14 in relation to the operating element 6. Therefore, the highest possible injection rate results in the third relative position 54. The energy which is required for rotating the entrainment element 14 in relation to the operating element 6 is minor. The injection rate is determined by the force stored in the spring 9 and by the friction forces which act between the mutually moving components.

The angle α of the latching edge 45 of the latching web 43 and the angle β of the latching edge 46 of the web 63 are identical in the embodiment. On account thereof, the latching depths $m_1$, $m_2$, $m_3$ are the same across the entire height c of the latching webs 43. In the case of dissimilar angles α, β, dissimilar latching depths m result in different portions of the latching web 43. The force exerted by the setting device 41 can be influenced by a suitable choice in terms of the configuration and the number of the latching webs 43.

Figure 30:
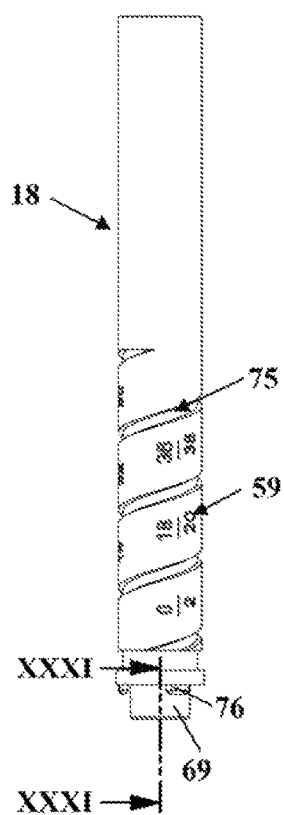
FIG. 30 shows a lateral view of a metering member of the injection device.
Figure 31:
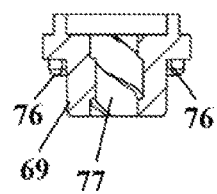
FIG. 31 shows a section along the line XXXI-XXXI in FIG. 30.
Figure 36:
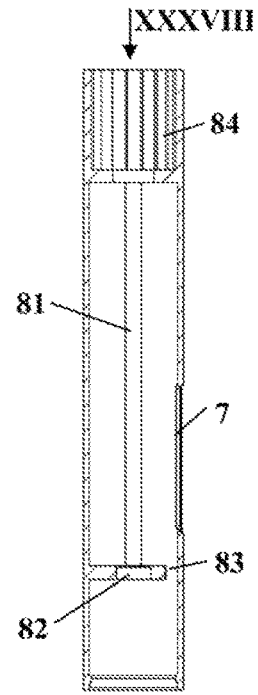
FIG. 36 shows a section along the line XXXVI-XXXVI in FIG. 35.
Figure 37:
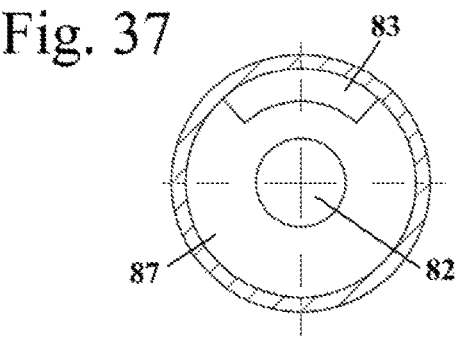
FIG. 37 shows a section along the line XXXVII-XXXVII in FIG. 35.

FIGS. 30 and 31 show the metering member 18 in detail. The metering member 18 has an external thread 75 which, conjointly with an internal thread 80 of the injection sleeve 17 (shown in FIG. 34), forms the first threaded connection 19. The metering member 18 has a bearing connector 69 by way of which the metering member 18 is rotatably mounted in a bearing opening 82 in the upper housing part 3 (FIGS. 36 and 37). The metering member 18 has bearing webs 76 which bear on that distal side of the housing wall 87 that has the bearing opening 82. The friction between the metering member 18 and the upper housing part 3 in the rotating movement of the metering member 18 is reduced. As is shown in FIG. 31, an internal thread 77 which, conjointly with the external thread 72 of the piston rod 12, forms the second threaded connection 22 is configured in the bearing connector 69 (FIG. 2).

Figure 32:
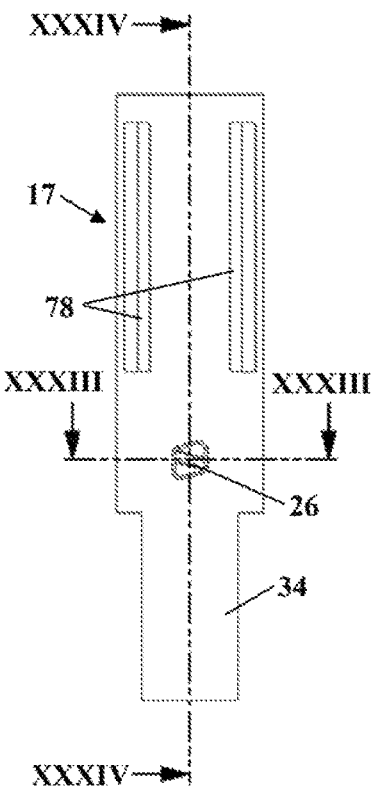
FIG. 32 shows a lateral view of an injection sleeve of the injection device.
Figure 33:
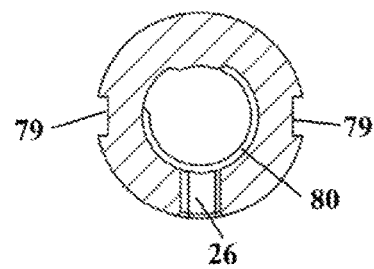
FIG. 33 shows a section along the line XXXIII-XXXIII in FIG. 32.
Figure 34:
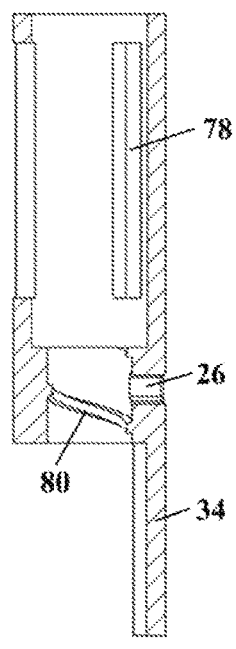
FIG. 34 shows a section along the line XXXIV-XXXIV in FIG. 32.

As is shown in FIG. 32, the injection sleeve 17 has clearances 78 which serve for reducing the weight. The opening 26 behind which the scale 59 of the metering member 18 (FIG. 30) is visible to the operator is also shown in FIGS. 32 to 34.

The injection sleeve 17 on the external circumference thereof has two guide grooves 79 which are disposed so as to be mutually opposite. Corresponding guide webs 81, one of which being visible in FIG. 36, are configured in the upper housing part 3. The guide webs 81 protrude into the guide grooves 79 and, on account thereof, guide in a rotationally fixed manner the injection sleeve 17 in the upper housing part 3 so as to be movable in the direction of the longitudinal axis 50.

As is shown in FIG. 37, the housing wall 87 beside the bearing opening 82 has a passage opening 83, the web 34 of the injection sleeve 17 protruding through the latter. The web 34 does not extend across the entire circumference of the injection sleeve 17 but only across the circumferential region in which the viewing window 7 is disposed. On account of the web 34, a small construction length of the injection device 1 is achieved at a sufficiently large adjustment range of the metering member 18. The metering member 18 rotates and the injection sleeve 17 is displaced in the axial direction when the dosage is being set. On account thereof, the set dosage is in each case visible through the opening 26.

As is shown in FIG. 38, the latching elements 85 of the latching mechanism 84 in the embodiment are configured so as to be non-symmetrical. The latching elements 85 interact with the latching elements 47 on the operating element 6 (FIG. 5). A dosage once set cannot be reduced by virtue of the non-symmetrical configuration of the latching elements. However, a reverse rotation of the operating element 6 for reducing a set dosage can also be possible by way of a corresponding configuration of the latching elements 85 and of the latching elements 47.

Clicking noises on account of the latching elements 47 and 85 are audible when setting a quantity of injection liquid to be squeezed out. As the operating element 6 and the upper housing part 3 are interconnected in a rotationally fixed manner when a quantity of injection liquid is being squeezed out, the clicking noises of the latching installation 35 are not audible when squeezing out injection liquid. Instead, clicking noises of the latching installation 42 of the setting device 41 are audible to the operator when squeezing out injection liquid. The latching installation 42 in the first latching position 52 herein generates louder clicking noises at a larger temporal interval. The further the operating element 6 is pushed in the proximal direction 31, the quieter the clicking noises and the more rapid the succession of the clicking noises. On account thereof, the injection rate is audible to the operator. The latching elements 85, conjointly with the latching elements 47, form the latching installation 35 when setting the dosage of injection liquid to be squeezed out. In the squeezing out of injection liquid, the latching elements 85 interact with the webs 38 and, conjointly with the latter, form the coupling 20 and connect the operating element 6 in a rotationally fixed manner to the upper housing part 3.

Figure 39:
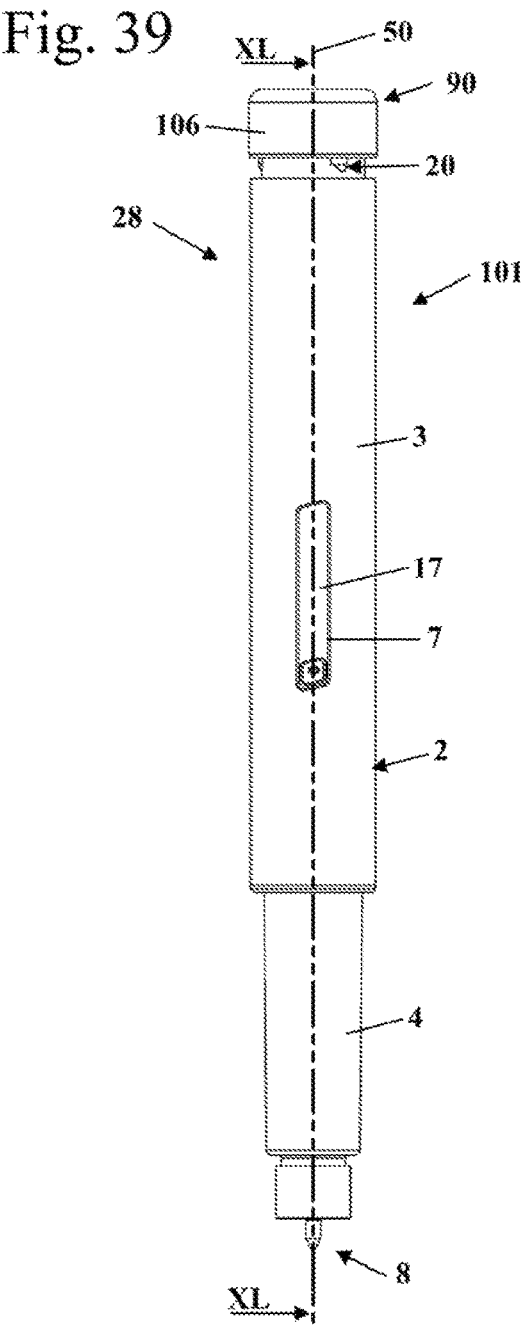
FIG. 39 shows a lateral view of a further injection device in the zero position.
Figure 40:
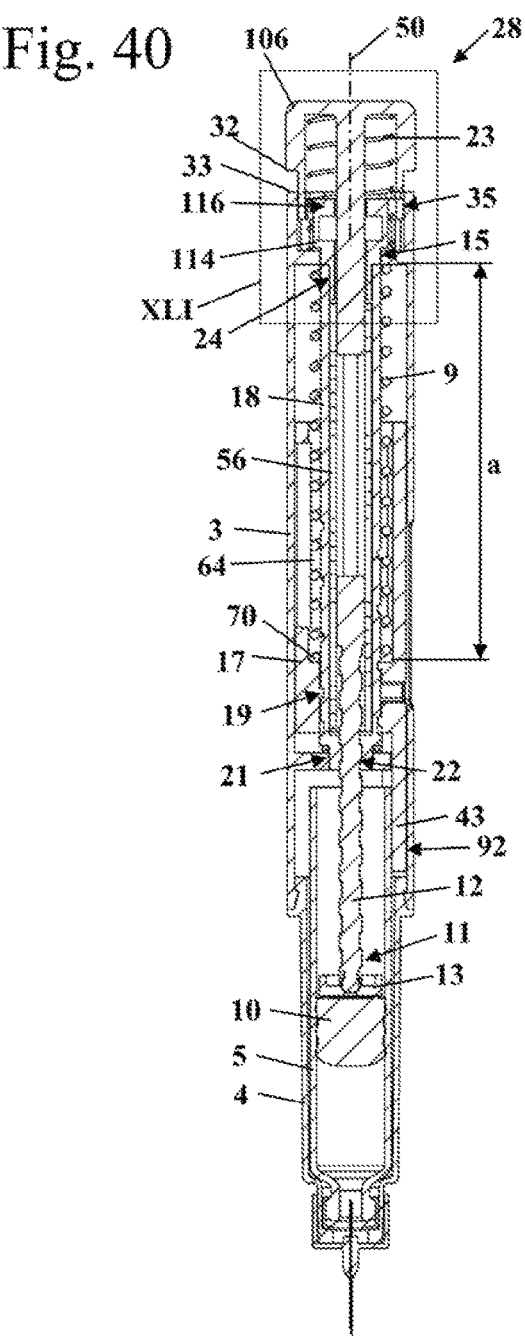
FIG. 40 shows a section along the line XL-XL in FIG. 39.

FIGS. 39 to 54 show an embodiment of an injection device 101, the construction of the latter corresponding substantially to that of the injection device 1 from the preceding figures. Equivalent components are identified by the same reference signs in all figures. The injection device 101 has a housing 2 having a viewing window 7 through which the injection sleeve 17 is visible. The injection device 101 has an operating element 106 that in the zero position 28 shown in FIGS. 39 and 40 is in a distal terminal position 90. The operating element 6 in this position can be held, for example, by a detent (not shown) that is configured on an entrainment element 114.

As is shown in FIG. 40, the injection device 101 differs from the injection device 1 substantially in terms of the configuration of the operating element 106 and of the entrainment element 114. The operating element 106 is pretensioned in the distal terminal position 90 thereof by a spring 23. A detent which is formed by a shoulder 32 of the operating element 106 and by a periphery 33 of the upper housing part 3 is formed between the operating element 106 and the upper housing part 3. A latching installation 35 acts between the operating element 106 and the upper housing part 3. The entrainment element 114 is mounted in the upper housing part 3 by way of a pivot bearing 15. A coupling 116 which in the distal terminal position 90 shown of the operating element 106 connects the operating element 106 in a rotationally fixed manner to the entrainment element 114 is formed between the entrainment element 114 and the operating element 106.

FIGS. 41 to 43 show the configuration of the operating element 106 and of the entrainment element 114 in detail. As is shown in FIG. 42, the upper housing part 3 in the distal end region thereof has a latching mechanism 84 which is formed by a multiplicity of latching elements 85. When setting a quantity of injection liquid to be squeezed out, the operating element 106 is to be rotated in a first rotation direction 88 in relation to the upper housing part 3. The latching elements 47 herein latch into the latching elements 85 of the upper housing part 3. Clicking noises that are audible to the operator are created herein. The entrainment element 114 has receptacles 117 which are configured as radially aligned slots, coupling webs 104 of the operating element 106 protruding into the receptacles 117. The coupling webs 104 can be configured so as to correspond to the latching webs 43 of the injection device 1. The coupling webs 104, conjointly with the receptacles 117, form the coupling 116.

As is shown in FIGS. 41 and 43, an interior space 110 is formed on that proximal side of the portion of the entrainment element 114 that has the receptacles 117, only the connector 66 of the operating element 106 protruding through the interior space 110 in the distal terminal position 90 shown of the operating element 106.

Figure 46:
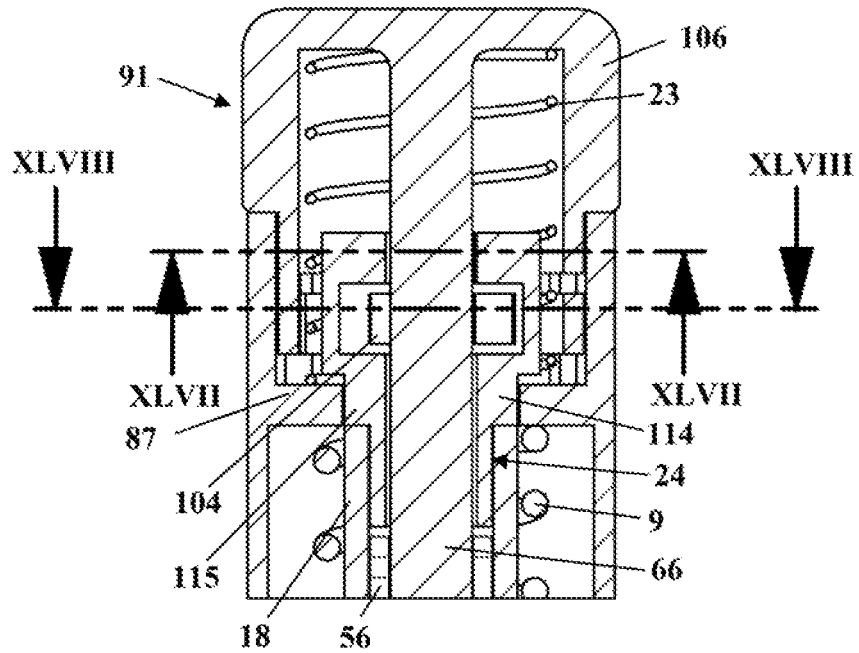
FIG. 46 shows the fragment XLVI from FIG. 45 in an enlarged illustration.
Figure 48:
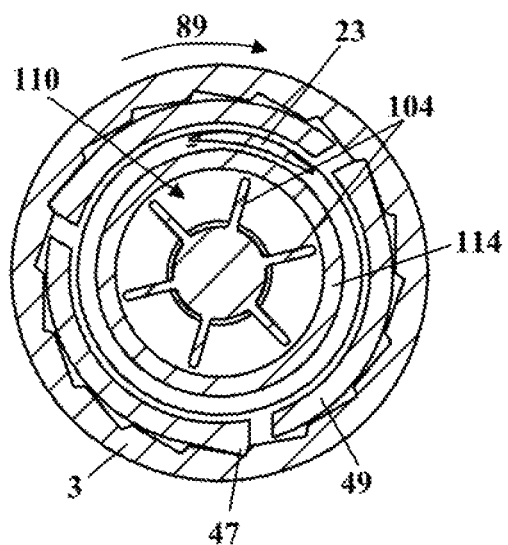
FIG. 48 shows a section along the line XLVIII-XLVIII in FIG. 46.

The injection device 101 is shown in a terminal position 102 in FIGS. 44 and 45. Upon setting a quantity of injection liquid to be squeezed out by rotating the operating element 106 in the first rotation direction 88, the operating element 106 was moved in the proximal direction 31 until the operating element 106 came to be in the proximal terminal position 91 thereof shown in FIGS. 44 and 45. The coupling 116 was released in the proximal movement of the operating element 106, and the entrainment element 114 was released and was able to rotate conjointly with the metering member 18 about the longitudinal central axis 50. The rotating movement was initiated by the energy which was stored in the spring 9 and which moved the injection sleeve 17 in the proximal direction 31. The shoulder 32 of the operating element 106 in the proximal terminal position 91 of the operating element 106 bears on the periphery 33 of the upper housing part 3 and forms the detent for the proximal terminal position 91. The coupling webs 104 of the operating element 106 are disposed in the interior space 110 of the entrainment element 114. As is shown in FIGS. 46 and 48, the coupling webs 104 can freely rotate in the interior space 110. Upon release of the coupling 116, the entrainment element 114, conjointly with the metering member 18, was able to rotate in the second rotation direction 89, and on account thereof was able to squeeze out the set dosage of injection liquid from the container 5.

Figure 47:
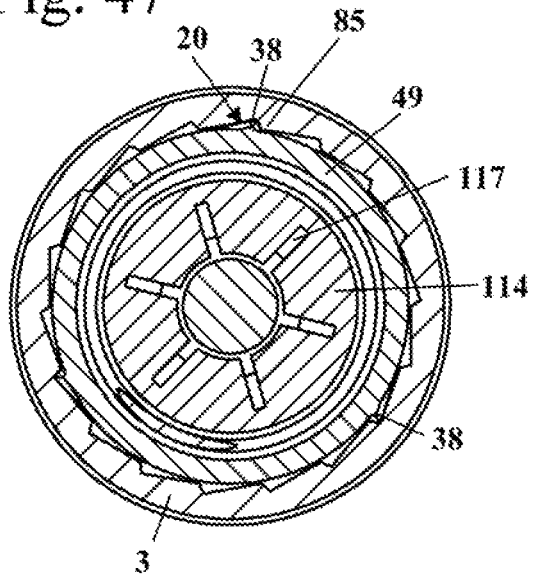
FIG. 47 shows a section along the line XLVII-XLVII in FIG. 46.

As is shown in FIG. 47, the webs 38 of the operating element 106 in the proximal terminal position 91 of the operating element 106 lie between the latching elements 85, and on account thereof connect the operating element 106 in a rotationally fixed manner to the upper housing part 3. The coupling webs 104 are not in the receptacles 117 but are completely in the interior space 110 such that a free rotation is possible. The webs 38, conjointly with the latching elements 85 of the latching mechanism 84, form the coupling 20.

Figure 49:
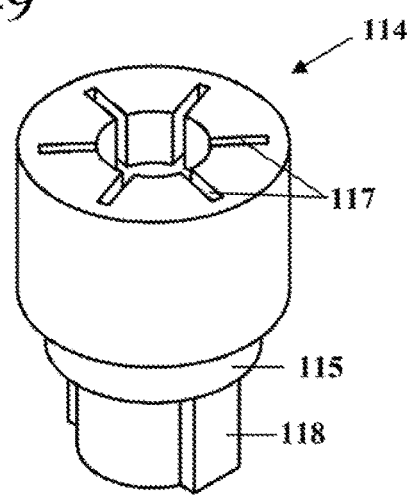
FIGS. 49 and 50 show perspective illustrations of the entrainment element of the injection device.
Figure 50:
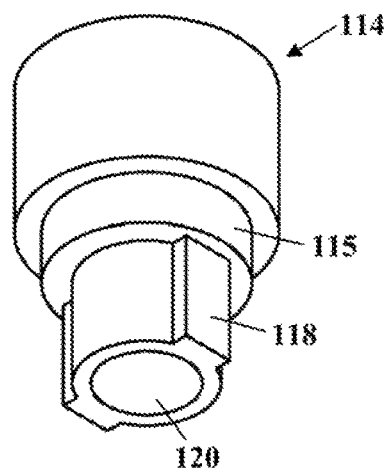
Figure 51:
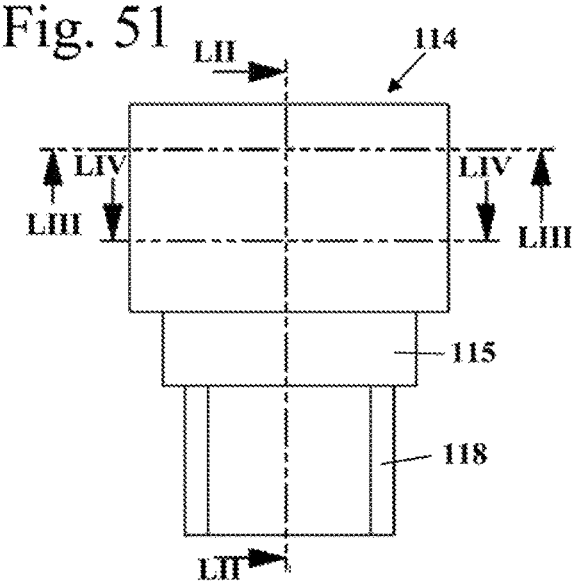
FIG. 51 shows a lateral view of the entrainment element.
Figure 52:
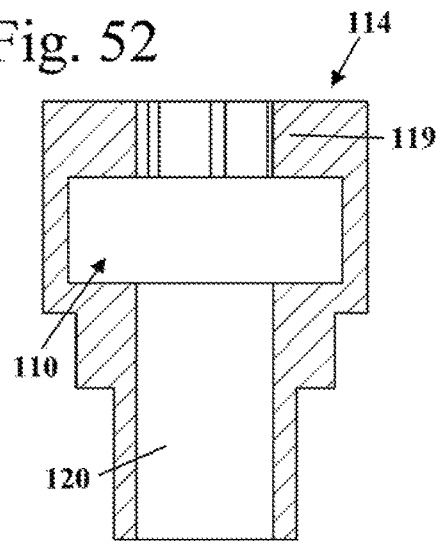
FIG. 52 shows a section along the line LII-LII in FIG. 51.
Figure 53:
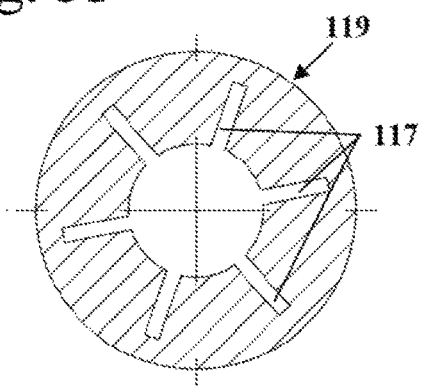
FIG. 53 shows a section along the line LIII-LIII in FIG. 51.
Figure 54:
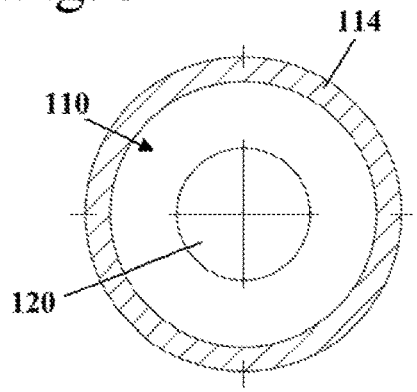
FIG. 54 shows a section along the line LIV-LIV in FIG. 51.

FIGS. 49 to 54 show the configuration of the entrainment element 114 in detail. As is shown in FIG. 49, the receptacles 117 are configured as radially running slots. The entrainment element 114 has a bearing portion 115 by way of which the former is rotatably mounted in the housing wall 87 (FIG. 46). As is shown in FIGS. 49 and 50, the entrainment element 114 in a proximal end region has securing webs 118 which serve for the rotationally fixed connection to the metering member 18. The entrainment element 114 is connected in a form-fitting manner to the metering member 18 by way of the securing webs 118. The entrainment element 114 centrally has an opening 120 through which the connector 66 of the operating element 106 protrudes. As is shown in FIGS. 52 and 53, the entrainment element 114 has a coupling portion 119 in which the receptacles 117 of the coupling 116 are configured. In the interior space 110 that adjoins the coupling portion 119 on the proximal side, the available internal diameter is chosen to be so large that the coupling webs 104 (FIG. 46) can freely rotate in the interior space 110.

In the case of the embodiment of an injection device 101 shown in FIGS. 39 to 54 the injection rate is not selectable by the operator but is determined by the energy stored in the spring 9, by the viscosity of the injection liquid, by the diameter of the injection needle, and by the friction of the plug 10 in relation to the container 5. In contrast, in the case of the injection device 1 the injection rate can be selected by the operator by way of a respective positioning of the operating element 6.

It is understood that the foregoing description is that of the preferred embodiments of the invention and that various changes and modifications may be made thereto without departing from the spirit and scope of the invention as defined in the appended claims.

What is claimed is:
1. An injection device comprising:
a housing defining a longitudinal central axis;
a metering member held in said housing so as to be rotatable and fixed axially along the longitudinal central axis;
an injection sleeve held so as to be rotationally fixed in relation to said housing and axially displaceable along the longitudinal central axis;
said metering member being disposed radially within said injection sleeve and connected to said injection sleeve via a first threaded connection;
the injection device defining a distal direction and a proximal direction;
wherein said metering member, when setting a dosage of injection liquid to be squeezed out, rotates in a first direction in relation to said housing and said injection sleeve by virtue of said first threaded connection moves in said distal direction;
wherein said metering member, when squeezing out a set dosage of injection liquid, rotates in a second direction opposite the first direction in relation to said housing and said injection sleeve by virtue of said first threaded connection moves in said proximal direction;

a spring having a first end and a second end;

said spring being supported via said first end in relation to said injection sleeve and via said second end in relation to said housing; and, wherein said spring, when squeezing out injection liquid, moves said injection sleeve in said proximal direction and on account thereof causes the set dosage of injection liquid to be squeezed out.

2. The injection device of claim 1, wherein said spring is configured as a compression spring.

3. The injection device of claim 1, wherein said spring by way of said first end is supported on said injection sleeve and by way of said second end is supported on said housing.

4. The injection device of claim 1, wherein:

said metering member has an external circumference; and, said spring is disposed on said external circumference of said metering member and at least partially in an annular space formed between the metering member and the injection sleeve.

5. The injection device of claim 4, further comprising:

a scale disposed on said external circumference of said metering member;

said housing having a viewing window;

said injection sleeve defining an opening which superposes said viewing window and through which said scale is visible; and, said injection sleeve having a portion which at a maximum dosage set covers a proximal region of the viewing window.

6. The injection device of claim 5, wherein said portion which at the maximum dosage set covers the proximal region of said viewing window is configured on a web of said injection sleeve which protrudes in said proximal direction.

7. The injection device of claim 6, further comprising:

a container having an injection liquid disposed therein;

the injection device defining a radial direction and a zero position;

said housing including an upper housing part; and, said container and said upper housing part defining a pocket therebetween in said radial direction into which said web protrudes in said zero position of the injection device.

8. The injection device of claim 6, wherein:

said housing has a housing wall on which a pivot bearing for said metering member is formed;

said housing wall defines a passage opening; and, said web protrudes through said passage opening in said housing wall onto a proximal side of said housing wall.

9. The injection device of claim 1, wherein said injection sleeve is disposed completely in said housing of the injection device.

10. The injection device of claim 1, further comprising:

an operating element which, when setting the dosage of injection liquid to be squeezed out, is connected in a rotationally fixed manner to the metering member via a first coupling; and, said operating element, when squeezing out the set dosage of injection liquid, being connected to said housing in a rotationally fixed manner via a second coupling and being rotatable in relation to said metering member.

11. The injection device of claim 10, wherein said operating element, when setting the dosage of injection liquid to be squeezed out, is in a distal terminal position and, in order for said first coupling to be released, is to be moved in said proximal direction.

12. The injection device of claim 4, further comprising:

a container;

a metering piston;

said metering piston being connected to said metering member via a second threaded connection;

said metering piston, when setting the dosage of injection liquid to be squeezed out, being connected in a rotationally fixed manner to said metering member and rotating conjointly with said metering member; and, said metering piston, when squeezing out the dosage of injection liquid to be squeezed out, being connected in a rotationally fixed manner to said housing and moving in the proximal direction by virtue of said second threaded connection.

* * * * *